United States Patent [19]

Seitz, Jr.

[11] Patent Number: 4,731,052

[45] Date of Patent: Mar. 15, 1988

[54] METHOD FOR REMOVING TISSUE AND LIVING ORGANISMS

[76] Inventor: H. Michael Seitz, Jr., 214 Airdale Rd., Rosemont, Pa. 19010

[21] Appl. No.: 3,133

[22] Filed: Jan. 14, 1987

[51] Int. Cl.$^4$ ............................................. A61M 31/00
[52] U.S. Cl. ........................................ 604/51; 604/34; 128/1 R
[58] Field of Search ...................... 604/51, 55, 28, 33, 604/34, DIG. 1; 128/1 R

[56] References Cited

U.S. PATENT DOCUMENTS

| | | | |
|---|---|---|---|
| 3,828,781 | 8/1974 | Rothman | 604/55 |
| 4,225,403 | 9/1980 | Lawson | 128/1 R |
| 4,299,221 | 11/1981 | Phillips et al. | 604/45 |
| 4,493,694 | 1/1985 | Wueinich | 604/22 |
| 4,526,573 | 7/1985 | Lester et al. | 604/119 |

FOREIGN PATENT DOCUMENTS

| | | | |
|---|---|---|---|
| 22463 | 9/1969 | Japan | 128/1 R |
| 2070436 | 9/1981 | United Kingdom | 128/1 R |

*Primary Examiner*—C. Fred Rosenbaum
*Assistant Examiner*—J. L. Kruter
*Attorney, Agent, or Firm*—Austin R. Miller

[57] ABSTRACT

A method for delicately and gently removing an egg from the human ovary for use in in vitro fertilization and a disposable or semi-disposable surgeon's aspirating and flushing valve for performing such a removal.

7 Claims, 11 Drawing Figures

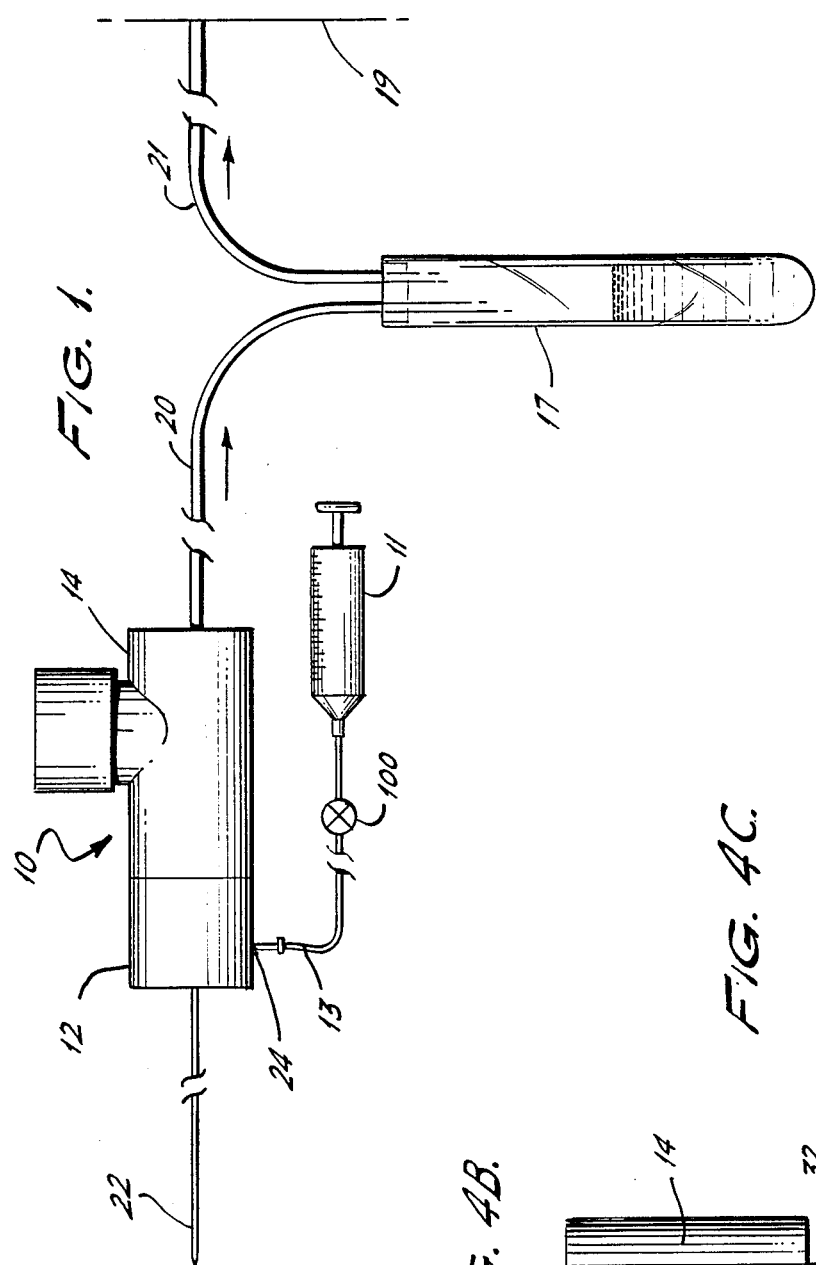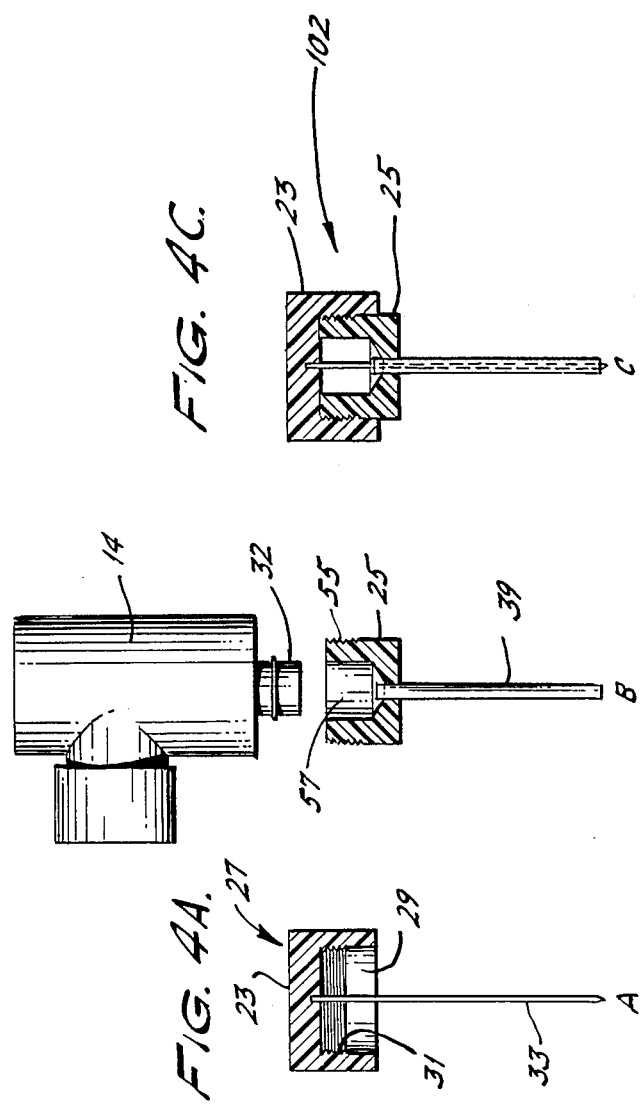

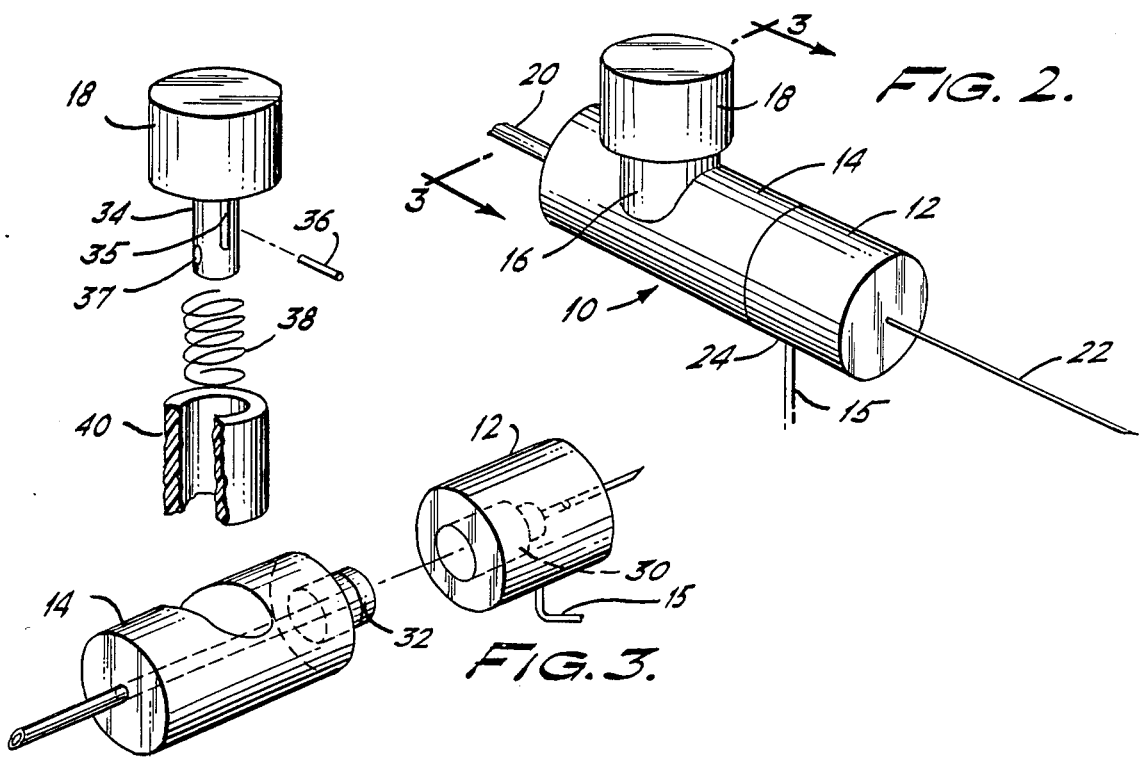
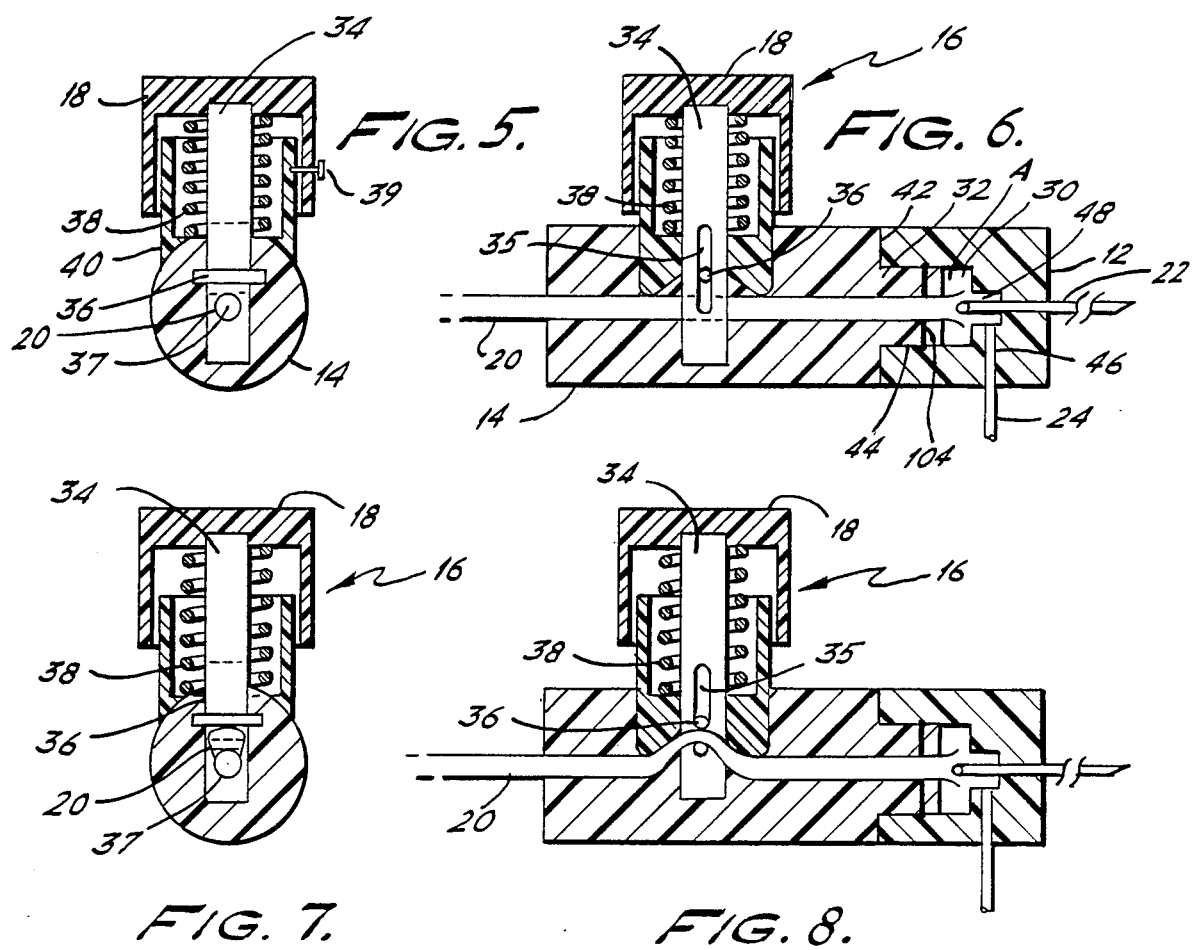

4,731,052

METHOD FOR REMOVING TISSUE AND LIVING ORGANISMS

BACKGROUND OF THE INVENTION

This invention relates to an aspiration and flushing device for use in a method of surgery for the removal of tissues, fluid and minute living organisms from the human body. Specifically, this invention grew out of a need for an efficient means of retrieving human eggs from the female ovary for use in in vitro fertilization (IVF) procedures. IVF is a recent approach which offers childless couples the opportunity to have children which otherwise would be unlikely or impossible.

FIELD OF INVENTION

IVF entails the surgical removal (aspiration) of human eggs (oocytes) from the female ovary, insemination of the retrieved oocytes and, at an appropriate time, transferring the oocytes back into the patient for possible implantation and pregnancy. In traditional procedures the oocytes are inseminated and allowed to remain in culture mediums in the laboratory for forty-eight hours after which time those that show evidence of fertilization are placed into the uterus of the patient. In certain instances the oocytes, after being inseminated in the laboratory, are immediately placed into the Fallopian tube of the patient where fertilization can take place and hopefully a pregnancy will result. This latter approach is known as the Gamete Intra-Fallopian Transfer (GIFT) procedure.

In systems requiring aspiration of fluids and/or tissues through a closed tubular system it is necessary to utilize a vacuum source to create suction. This can either be manually created as with a large hypodermic syringe or it can be supplied through a central mechanical source which is available in most hospital units. It is desirable that the force of this suction can be measured and controlled. In delicate operations such as in IVF oocyte recovery, it is of paramount importance to have elected suction actuated by the surgeon when attempting to retrieve a human egg. It is essential that suction be applied at the precise moment the compartment containing the egg (follicle) is punctured with the aspirating device. It has been found that delegating the activation of suction to another person frequently is undesirable and unworkable. It should be stated that the compartment that houses the human egg is a fluid filled structure which is under pressure, and if puncture of this structure is made asyncronously upon the activation of suction, the follicular contents escape and the egg is frequently not recovered. The human egg is enveloped in many layers of cells (cumulus) which are extremely important to the nourishment, growth and development of the egg and should not be removed or destroyed.

In addition to aspiration, some situations require the introduction of a washing or flushing solution into either the general vicinity of the aspirated area or into the exact location where aspiration has occurred. As in the case where an egg is to be removed, it is desirable for a flushing solution to be introduced into the same point of aspiration, after aspiration has occurred in order to redistend or refill the evacuated compartment (follicle) so that a second attempt at recovery of the egg can be made without additional puncture of the follicle. Frequently the egg is not removed at the time of initial aspiration but is recovered in subsequent washings.

There have been several problems that have confronted surgeons in trying to find suitable apparatus to perform such delicate types of surgery. For example, because target follicles are small, it is potentially harmful to the tissue to have multiple puncture sites into a follicle. It is also undesirable to use one comparatively large aspirating device such as the double-lumen needle because it is traumatic to the follicle and increases the risk of bleeding. The inner diameter of the aspirating device and collecting system is very important. If it is too small, the egg can easily be divested of the vital cumulus cells surrounding and protecting the egg, which would diminish the success of the procedure. Moreover, the small inner diameter tends to increase the speed of passage of the aspirated contents and has the potential for injury to the egg. The ideal aspirating system should be one in which the surgeon can control the suction with fingertip action, provide a means to introduce flushing solution through the same portal used for aspiration, and the aspirating device be of adequate diameter so as not to damage the contents of the aspirate.

The need for selective suction has resulted in an inability to find a suitable apparatus which precisely and immediately controls suction as the surgeon desires. Since the procedure occurs over a period of time, it is preferable that the apparatus be capable of easily remaining completely closed. The apparatus should be flexible in operation so as to easily and very quickly shift from a suction mode, to no operation, to a flushing mode and back to a suction mode. This quick shifting of modes required a quick reaction from the operator which means that the operating surgeon himself or herself should operate the control mechanism.

Because it is highly desirable that the surgeon personally actuate the suction, it is preferred that the aspiration control device be designed to require as little conscious thought as possible to manipulate and not be contrary to natural movement. The surgeon's mind should concentrate on removing the target tissue or fluid and not on how the on-off switch of the aspirating control device works.

It is desirable that the apparatus be of a design so as not to injure the tissue or to allow it to lodge somewhere in the device. Such delicacy of design precludes a collection system with an inordinately small inside diameter, sharp corners, jagged edges or obstructions in the passageway through which the tissue flows.

DESCRIPTION OF THE PRIOR ART

U.S. Pat. No. 4,299,221 discloses an irrigation and suction handpiece having three separate passageways, one each for pressurized air, vacuum suction and an irrigant liquid. The passageways for the vacuum and the irrigant extend to the target area, while the pressurized air passageway terminates short of the target. A valve means is provided on the handpiece for the irrigant.

This device is undesirable for delicate surgical techniques for several reasons. There are separate passageways for aspiration and flushing which is overly traumatic for a small target. The passageways do not terminate at the same point, which requires unwanted needle manipulation when shifting from an aspiration mode to a flushing mode. Also, there is no valve to control aspiration on the device itself. Having such a valve is highly preferred for direct surgeon's control.

U.S. Pat. No. 4,493,694 discloses a surgical preaspirator, which supplies an irrigation fluid by way of an outer concentric passageway to the end of an inner concentric passageway to assist in aspirating through the inner concentric passageway various body tissues.

However, this device does not have a valve to control aspiration located thereon, and it does not introduce the irrigant into the target area. The irrigation fluid does not travel outside of the device to flush the target, but instead, assists the aspirated tissues along the suction passageway.

U.S. Pat. No. 4,526,573 discloses suction-irrigation equipment with a control valve. The device has parallel bores, one connected to a vacuum source and the other to an irrigating fluid. A valve assembly having two inlet conduits is attached to the bores, one inlet to the suction bore, and one inlet to the irrigation bore. An outlet conduit can be connected to one or the other of the bores by displacing a valve member.

While the device is disclosed as having a neutral position with no suction or irrigation, the valve member must be precisely placed in order to establish the neutral position, and the operator must maintain the position, or the spring actuated valve member will automatically displace it to the suction mode. This runs counter to the optimal arrangement of producing aspiration upon shifting or depressing the valve member, and is therefore undesirable.

The internal design of the valve assembly is such that it tends to subject the aspirated tissue and fluid to traversing sharp corners and much turbulence. There is also the possibility that if the valve member is moved as the tissue passes through the valve chamber that it could be caught in the valve member flanges, and either be damaged, crushed or permanently caught within.

OBJECTS OF THE INVENTION

Thus, it is an object of the present invention to provide a disposable or semi-disposable aspiration and flushing device and method which allows a surgeon to personally control aspiration through a valve located on the device, which valve and method permits aspiration when depressed by the surgeon and interrupts aspiration upon release.

It is another object of the present invention to provide an aspiration and flushing device and method which permits aspiration and the introduction of a flushing fluid at the same point through a single small hollow needle to minimize the size of the puncture in the organ or tissue to be aspirated so as to reduce unwanted bleeding, and to reduce the amount of manipulation of the needle after insertion.

It is an important object of the present invention to provide an aspiration and flushing device and method to pierce a follicle in a human female and retrieve an egg therefrom for artificial insemination, with the internal design of the device being so constructed as to provide a clear passageway for the egg to travel without obstruction or turbulence so that the egg is not lost, damaged or destroyed.

It is another important object of the present invention to provide an aspiration and flushing device which can quickly and easily be connected to an existing vacuum source and can handily be assembled for one time use, thereby further eliminating the element of infectious disease potential and insuring the sharpness of the needle.

It is still a further object of the present invention to provide a special cannula-trocar extension of the present invention in which the application of vacuum is utilized to provide the introduction of the device into the human body and also to serve as a holding or grasping means when suction is applied to the main body of the device in order to grasp and hold tissues, remove excess blood and fluid from a cavity as well as provide a portal of entry through which specialized surgical instruments can be introduced.

Other objects and advantages of the present invention will become readily apparent to those skilled in the art from the drawings, detailed descriptions of the preferred embodiments and the appended claims.

SUMMARY OF THE INVENTION

The present invention provides a method for delicately and gently removing an egg from the human ovary for use in in vitro fertilization and a device for performing such a removal. The surgeon's aspirating and flushing valve has a first body with a needle extending therefrom for insertion into the human ovary for removal of an egg and the introduction of flushing fluid. The first body also contains a passageway leading to a flushing fluid chamber where flushing fluid is introduced into the needle. When aspiration is being performed, the flushing portal is open while the aspirating device is in the closed position. There is a second body containing flexible tubing connectable to a vacuum means which extends into the flushing fluid chamber and surrounds the end of the needle without contacting it. The flexible tubing surrounding the needle is of slightly greater outside diameter than the needle and therefore creates an umbrella effect. The second body contains a pinching valve which when depressed allows suction through the flexible tube and the needle in a non-tortuous path, and when released pinches the flexible tubing, thereby preventing suction and allowing flushing fluid to be introduced through the passageway, the flushing chamber and down into the needle. When the flushing portal is closed and suction is activated, the tissue and fluid being aspirated flow freely through the flexible tubing into a test tube trap where the contents are retrieved. The construction of the terminal portion of the second body permits rapid changing of needles, and when fitted into the special cannula serves as a suction holding device.

The semi-disposable unit possesses all advantages of the disposable unit and is of similar construction with the addition of a quickly assembled reusable housing having one end surrounding a portion of the first body approximate the flushing fluid chamber, and having another end surrounding a portion of the second body. The first and second body portions are disposed of after single use, with the entire unit being ideally suited for trans-vaginal ultrasound recovery wherein IVF procedures are performed without a trocar-cannula or a tissue holding mechanism.

BRIEF DESCRIPTION OF THE DRAWINGS

FIG. 1 is a schematic view of a system of apparatus for removing tissues, fluid and eggs in accordance with the present invention.

FIG. 2 is a plan view in perspective of one embodiment of an aspiration and flushing device in accordance with the present invention.

FIG. 3 shows a perspective view of one embodiment of the present invention, broken apart for ease of understanding.

FIG. 4 shows a side plan view of the valve portion of one embodiment of an aspiration and flushing device along with side sectional views of an interchangeable cannula means and a puncture needle, as utilized in accordance with the present invention.

FIG. 5 is an end view of an aspiration and flushing device shown in section generally along the 3—3 line from FIG. 2, with the valve in the "on" position.

FIG. 6 shows a side sectional view of an aspiration and flushing device in accordance with the present invention with the valve in the "on" position.

FIG. 7 is an end sectional view of the apparatus from FIG. 6 with the valve in the "off" position.

FIG. 8 shows a side sectional view of the apparatus from FIG. 6 with the valve in the "off" position.

Figure 9:
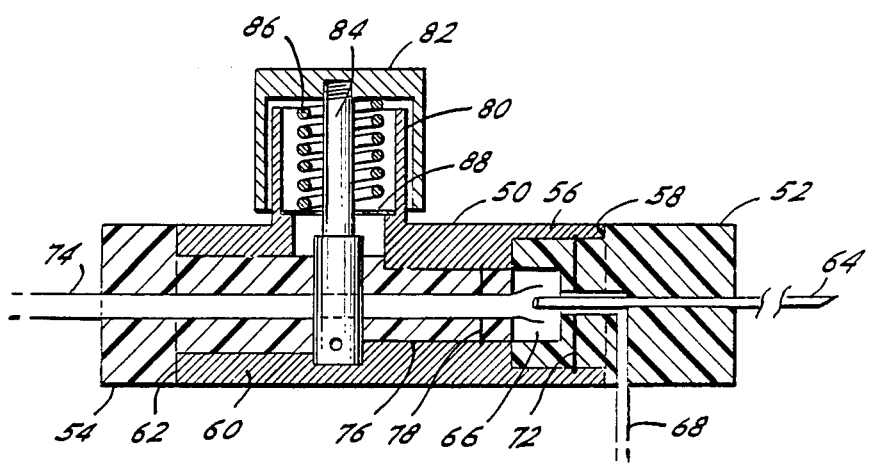
FIG. 9 shows a side sectional view of an aspiration and flushing device in accordance with the present invention with the valve in the "on" position.

DETAILED DESCRIPTION OF PREFERRED EMBODIMENTS OF THE INVENTION AND THE BEST MODE CONTEMPLATED FOR PRACRICE THEREOF

A system for collecting human eggs in accordance with the method of the invention is shown in FIG. 1. Device 10 comprises primarily a first body portion 12 and a second body portion 14. Pointed needle 22 for insertion into a human body connects to first body portion 12. Syringe 11 for the introduction of flushing fluid connects to first body portion 12 at syringe portal 24 by way of flexible tubing 13. Flexible tube 13 is provided with valve 100. Flexible tubing 20 exits second body portion 14 and connects to collection trap 17, which in turn is connected to a continuous vacuum source in wall 19 by way of flexible tubing 21.

An aspiration and flushing device 10 for removing small organisms is shown in FIG. 2. Device 10 has a first body portion 12 and a second body portion 14. Extending from second body portion 14 is a valve 16 having lever 18. Also extending from second body portion 14 is flexible tubing 20. First body portion 12 has a needle 22 extending outwardly from one end, and a syringe portal 24 (as previously described) at the side, with flexible tubing 15 extending therefrom.

First body portion 12 is shown broken away from second body portion 14 in FIG. 3. Dashed lines define a flushing fluid chamber 30 in first body portion 12. Needle 22 and flexible tubing 15 extend outwardly from first body portion 12. Flexible tube 20 extends outwardly from second body portion 14, and also extends interiorly through its length as defined by dashed lines. Extending outwardly from the outer end of second body portion 14 is extension 32.

Valve lever 18 has a downwardly extending plunger 34 with a slot 35 through which pinching pin 36 extends. Spring 38 surrounds plunger 34 and is in turn surrounded by valve housing 40.

In FIG. 4A, trocar body portion 23 has an extension receiving end 27 and a cannula body receiving end 29 with threads 31. Trocar 33 extends from trocar body portion 23 by way of cannula body receiving end 29. In FIG. 4B, second body portion 14 and extension 32 are positioned to receive cannula body portion 25. Cannula body portion 25 has threads 55 on the outside and a trocar body extension receiving space 57 on the inside. Cannula 39 extends therefrom. FIG. 4C shows cannula body portion 25 and trocar body portion 22 threaded together.

FIG. 5 shows lever 18 in a depressed position and being locked in place by lock pin 39, with spring 38 being compressed inside housing 40. Plunger 34 is similarly fully depressed with tubing 20 extending therethrough by way of hole 37. Pinching pin 36 is fixed within second body portion 14.

FIG. 6 shows valve 16 similarly disposed as in FIG. 5. Lever 18 and plunger 34 are depressed, with spring 38 being compressed. Pinching pin 36 extends through slot 35 and is adjacent tubing 20 which extends through hole 37 (see FIG. 5).

First body portion 12 and second body portion 14 are connected together at end surface 42 and cylindrical surface 44 of extension 32. Extension 32 extends into first body portion 12 and forms flushing fluid chamber 30. O-ring 104 extends around extension 32. Tubing 20 extends into fluid flushing chamber 30 and surrounds a portion of the end of needle 22 which also extends into fluid flushing chamber 30. Syringe portal 24 connects into fluid passageway 46 which connects into a portion 48 of fluid flushing chamber 30.

FIG. 7 shows valve 16 in a released position with lever 18 and plunger 34 raised upwardly, and spring 38 extended. Stationary pinching pin 36 pinches tube 20 within hole 37 as plunger 34 is raised. FIG. 8 shows valve 16 similarly disposed as in FIG. 7. Lever 18 and plunger 34 are released with spring 38 extended. Pinching pin 36 extends through slot 35 and pinches tubing 20 which extends through raised hole 37 (see FIG. 3).

FIG. 9 shows another embodiment of an aspiration and flushing device, a portion of which is non-disposable, with the remainder being disposable. Housing 50 surrounds portions of a first body portion 52 and a second body portion 54. Lip 56 on housing 50 surrounds first body portion 52 along groove 58. Lip 60 surrounds second body portion 54 along groove 62. First body portion 52 has a needle 64 extending outwardly from one end and a fluid flushing chamber 66 bored in the other end. Syringe portal 68 extends outwardly from a fluid flushing passageway 70 leading into fluid flushing chamber 66. O-ring 72 provides a seal between lip 56 and groove 58.

Flexible tubing 74 extends through second body portion 54 and extension 76, and into fluid flushing chamber 66. The end of tubing 74 within fluid flushing chamber 66 surrounds the end of needle 64 which extends into fluid flushing chamber 66. O-ring 78 provides a seal between housing 50 and extension 76. Valve housing 80 extends through surrounding spring 86 and washer 88 into housing 50.

Figure 10:
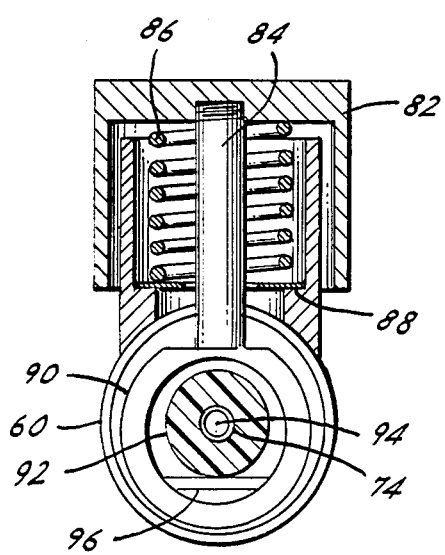
FIG. 10 is an end view of another embodiment of an aspiration and flushing device in the "on" position.

FIG. 10 shows the valve of FIG. 9 similarly disposed in the depressed position. Lever 82 and plunger 84 are in the downward position with spring 86 compressed against washer 88. Plunger head 90 is surrounded by housing 60 and in turn surrounds an inner portion 92 of second body portion 54 (see also FIG. 9). Flexible tubing 74 extends through hole 94. Pinching pin 96 is held within plunger head 90 and below portion 92.

Figure 11:
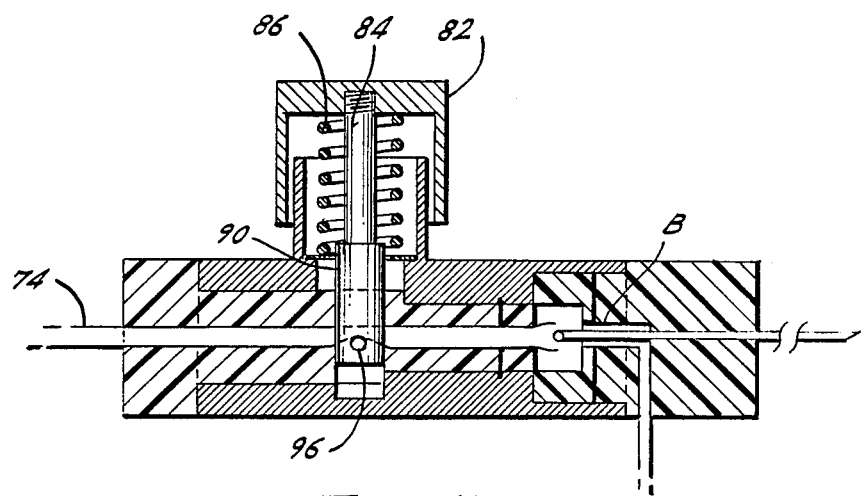
FIG. 11 is a side sectional view of the apparatus from FIG. 9 with the valve in the "off" position.

FIG. 11 shows the device of FIGS. 9 and 10 with the valve in the released position. Lever 82 and plunger 84 are in an upward position with spring 86 extended.

Plunger head 90 is also pulled upward by plunger 84. Pinching pin 96 is raised upward and pinches tubing 74.

Referring now to FIG. 2, device 10 can be employed in a wide variety of surgical situations and procedures where it is desirable to aspirate and/or flush tissues and/or fluids. It has been found that the present invention is particularly suited for surgical procedures involving IVF either alone or in combination with other devices such as those shown in FIGS. 1 and 4, for example. Hereinbelow, the operation of the apparatus of the present invention will be specifically explained, based on the type of surgical procedure for which it has been found to be particularly suited, although it should be recognized that the apparatus utilized in accordance with the present invention can be employed in other micro-type surgical procedures.

Isolating and removing an egg from a follicle prior to artificially inseminating it requires a delicate and precise procedure which does not damage either the patient or the target egg. The procedure of the present invention typically involves first introducing a laparoscope in the abdominal cavity of the female for viewing the ovary. Then a hollow cannula with a valving apparatus in accordance with the present invention is introduced nearby and connected to conventional suction means and a trap for collecting fluids and tissues. It is alternatively possible to utilize a vaginally introduced ultrasound probe head for viewing. It has further been found that the cannula may be vaginally introduced along with the ultrasound probe head, if desired.

Before beginning this particular procedure, one embodiment of device 10 is first assembled and connected as shown in FIG. 1. Referring to FIG. 4, second body portion 14 is fixed to trocar/cannula body portion 25. The preferred method is by simply sliding trocar body portion 25 onto extension 32 and then threading on cannula body portion 25. Depending upon the size of the available conduit to the vacuum source, different sizes of flexible tubing 20 may be provided. Similarly, the surgeon may desire different sizes of needles 22, cannulas 39 or trocars 33. Having separate body portions such as those alternatively illustrated allows for increased interchangeability and flexibility.

A laparoscope is introduced into the patient generally through the navel. The laparoscope can be utilized to view the abdominal region in general, and to locate a suitable follicle. A grasping device is then introduced into the patient generally above the bladder.

A surgeon's aspiration and flushing device 10 according to the present invention is introduced generally either to the left or right of the grasping device by using needle 22 as a puncture mechanism. Device 10 can also be introduced by way of a trocar/cannula unit 102. Trocar 33 (FIG. 4A) serves as a puncturing piece for cannula 39. Trocar 33 is then removed and extension 32 inserted into receiving space 57 as shown in FIG. 4B. Needle 22/cannula 39 can have several types of tips including being blunt nosed, pointed or having a scalpel edge. Flexible tubing 20 (FIG. 1) is connected to a continuous vacuum source, and flexible tubing 13 can be provided with a syringe for future introduction of flushing fluid or irrigant.

After insertion of needle 22 into the patient, the surgeon locates a suitable follicle on an ovary for penetration in order to extract an egg. The grasping device is employed to grasp an avascular ligament residing close to the ovary in order to steady it. With additional suction capabilities, the surgeon can manipulate and separate the fingers of the Fallopian tube for better viewing. Needle 22 punctures the follicle to gain access to an egg. The opening at the end of the needle 22 is used to aspirate the egg out of the patient. As controlled by locking pin 39 in FIG. 5, valve lever 18 is maintained in a depressed position in order to avoid crimping tube 20 prior to use. Prior to the start of the procedure, the surgeon removes locking pin 39 to avoid unwanted premature aspiration. When the surgeon desires to aspirate the egg, he or she presses on lever 18.

Pyschologically, it has been found that the preferred valve or "on-off" mechanism is one which actuates suction when depressed, and terminates suction upon release. This requirement dictates against prior art designs since it is far easier to construct a valve which terminates flow when depressed and actuates flow upon release. Before pressing lever 18, pinching pin 36 pinches tubing 20 which prevents aspiration, as shown in FIG. 8. As the surgeon presses on lever 18, tubing 20 is released as shown in FIG. 7.

Upon release of tubing 20, aspiration is actuated, and fluids and the egg are sucked into needle 22. From needle 22, the egg and accompanying fluids pass directly and atraumatically into tubing 20. This atraumatic passage is most critical because of the delicateness of the egg in this instance, and because of the delicateness of body tissue in general. In order to insure that the egg is removed, the aspiration and flushing device 10 permits such atraumatic passage because the end of tubing 20, which extends beyond extension 32 and into fluid flushing chamber 30, surrounds the end of needle 22 which extends into fluid flushing chamber 30. The end of tubing 20, is sometimes flared as shown in FIGS. 6 and 8, as is the end of tubing 74 appearing in FIGS. 9 and 11, although flaring is not always necessary. The need for flaring typically arises upon the usage of a large gauge needle 22 as compared to the gauge of flexible tubing 20 or 74. Smaller gauge needles 22 generally do not require flaring, although flaring does not impair the effectiveness of the device.

It is however, important that whether or not tubing 20 or 74 is flared, that the end of tubing 20 or 74 extend at least to the end of needle 22 or 64 and preferably to extend over the end of needle 22 or 64 to form an "umbrella" effect. The overlapping of ends should preferably be at least 1/16 of an inch, although 1/16 of an inch is not critical. This insures that fluids, eggs and tissues passing between the needle and the tubing do so atraumatically. If there is no umbrella effect, as is the case with prior art devices, then there is the tendency for the tissue and/or fluids to escape either temporarily or permanently into fluid flushing chamber 30. Even if recovered after such an escape, any tissue or egg would be subjected to serve turbulence and possible damage.

It is important that a space remain between the ends of tubing 20 and needle 22 despite the overlapping requirement. Space is needed in order for flushing fluid or irrigant to be introduced into needle 22. When aspirated, the follicle collapses and should be redistended. Such redistending is accomplished by introducing irrigant through needle 22 and back to the follicle without ever having removed needle 22.

In order to introduce irrigant through needle 22, a syringe is connected to syringe portal 24. As shown in FIG. 6, syringe portal 24 leads to passageway 46 within first body portion 12 and is connected to fluid flushing chamber 30. It is possible to have alternative designs of connection between passageway 24 and fluid flushing chamber 30 as shown at Point A in FIG. 6, and between passageway 70 and fluid flushing chamber 66 at Point B in FIG. 11.

From Point A, irrigant flows into fluid flushing chamber 30, and between the space between the end of needle 22 and tubing 20 within fluid flushing chamber 30 where it is then free to flow out of the other end of needle 22 and into the follicle. Small amounts of irrigant may also enter tubing 20, but pinching pin 36 as shown in FIGS. 7 and 8 prevents any flow past plunger 34. Valve 100 prevents passage of aspirated fluids or tissues from travelling through tubing 13.

Aspiration and fluid flushing device 10 shown in FIGS. 1 to 8 is primarily intended for completely disposable use. First body portion 12 and second body portion 14 can be fixed or glued together prior to use or may remain secured only by the sealing effect of the O-ring. Device 10 may be fabricated from any suitable material, although PVC (polyvinylchloride) plastic is preferred for a variety of reasons, including machineability, weight, cost, and lack of toxicity.

The embodiment depicted in FIGS. 9 to 11 is primarily intended to be partly disposable and partly reusable. The device is assembled from three pieces; housing 50, first body portion 52 and second body portion 54 by the surgeon. First body portion 52 is slipped inside lip 56, with O-ring 72 forming a seal. Similarly, second body portion 54 is slipped inside lip 60, with O-ring 78 forming a seal. However, in order for portion 92 (see FIG. 10) and extension 76 to slide completely within housing 50, plunger 84 and plunger head 90 must be fully depressed in order to allow clearance of portion 92 through the hole in plunger head 90. As with the completely disposable embodiment, the disposable portions of the semi-disposable embodiment may be made of any suitable material, perferrably PVC plastic or the like. Housing 50 should be constructed of a rigid material which can withstand the rigors of repeated sterilization. Stainless steel is preferred.

Thus, an aspiration and flushing procedure practiced in accordance with the method of the present invention allows a surgeon to personally and directly control gentle aspiration of an egg through a needle by depressing a valve member located on the device and to interrupt aspiration upon release of the value member. It also permits the introduction of an irrigating fluid directly into the device so as to be injected through a needle to the exact location of irrigation so as to reduce minimize traumatic manipulation of the needle after insertion. The device can be either completely or partially disposable and can be easily assembled for use with a vacuum source and other surgical devices if desired, and aspirates tissues, eggs and/or fluids without damaging them.

Although this invention has been described in connection with specific forms and embodiments thereof, it will be appreciated that a wide array of equivalents may be substituted for the specific elements shown and described herein without departing from the spirit and scope of this invention as described in the appended claims.

I claim:

1. In a method of artificially inseminating an egg, of the type wherein viewing means are applied to a female patient for locating and viewing at least one ovary to remove an egg from a follicle thereon by suction with needle means, said needle having suction means attached thereto, the steps comprising:
    (a) while viewing said follicle introducing a needle portion of an aspiration and flushing means into the abdominal cavity, invading the follicle and aspirating the egg therefrom, removing said egg by aspiration while providing a smooth, non-turbulent and continuous pathway for said egg to prevent egg damage during aspiration, introducing flushing fluid through said needle portion by way of a syringe passageway, said aspiration and flushing steps including actuating aspiration upon depression of a valve means controlling said aspiration and ceasing aspiration upon release of said valve means;
    (b) said invasion of said follicle being accompanied by puncturing said follicle with said needle;
    (c) said aspiration being accompanied by pressing valve means connected to said suction means and actuating suction through said needle to evacuate said follicle;
    (d) said step of introducing flushing fluid into said follicle being accomplished through said needle portion from a syringe passageway to redistend said follicle; and
    (e) repeating steps (c) and (d) until an egg is evacuated from said follicle.

2. The method defined in claim 1 further comprising the steps of:
    introducing grasping means into said human generally above her bladder prior to puncturing said follicle; and
    grasping with said grasping means a vascular ligament proximate said ovary for steadying thereof.

3. The method defined in claim 2 wherein said grasping means comprises a hollow needle having separate valved suction means attached thereto.

4. The method as defined in claim 1 wherein said viewing means are introduced generally through her navel.

5. The method as defined in claim 1 wherein said viewing means are introduced vaginally.

6. The method as defined in claim 1 wherein said needle means are introduced generally above and either to the left or right of her bladder.

7. The method as defined in claim 1 wherein said needle means are introduced vaginally.

* * * * *